(12) United States Patent
Jackson (10) Patent No.: US 6,942,698 B1
(45) Date of Patent: Sep. 13, 2005

(54) SPINAL FUSION INTERBODY SPACER

(76) Inventor: Roger P. Jackson, 4706 W. 86th St., Prairie Village, KS (US) 66207

( * ) Notice: Subject to any disclaimer, the term of this patent is extended or adjusted under 35 U.S.C. 154(b) by 0 days.

(21) Appl. No.: 10/831,461

(22) Filed: Apr. 23, 2004

(51) Int. Cl.[7] ............................ A61F 2/44; A61B 17/56
(52) U.S. Cl. ...................................... 623/17.16; 606/61
(58) Field of Search ......................... 623/17.11–17.16; 606/61, 69–74

(56) References Cited

U.S. PATENT DOCUMENTS

| | | | |
|---|---|---|---|
| 4,349,921 A | * | 9/1982 | Kuntz ..................... 623/17.16 |
| 4,834,757 A | | 5/1989 | Brantigan |
| 5,139,527 A | | 8/1992 | Redl et al. |
| 5,425,772 A | | 6/1995 | Brantigan |
| 5,443,514 A | | 8/1995 | Steffee |
| 5,458,638 A | | 10/1995 | Kuslich et al. |
| 5,489,308 A | | 2/1996 | Kuslich et al. |
| 5,554,191 A | | 9/1996 | Lahille et al. |
| 5,609,636 A | | 3/1997 | Kohrs et al. |
| 5,658,337 A | | 8/1997 | Korhs et al. |
| 5,665,122 A | | 9/1997 | Kambin |
| 5,669,909 A | | 9/1997 | Zdeblick et al. |
| 5,681,135 A | | 10/1997 | Simonson |
| 5,693,100 A | | 12/1997 | Pisharodi |
| 5,716,355 A | | 2/1998 | Jackson et al. |
| 5,716,415 A | | 2/1998 | Steffee |
| 5,782,919 A | | 7/1998 | Zdeblick et al. |
| 5,865,847 A | | 2/1999 | Kohrs et al. |
| 5,904,719 A | | 5/1999 | Errico et al. |
| 5,941,880 A | | 8/1999 | Errico et al. |
| 5,968,098 A | | 10/1999 | Winslow |
| 5,980,522 A | | 11/1999 | Koros et al. |
| 6,053,916 A | | 4/2000 | Moore |
| 6,102,950 A | | 8/2000 | Vaccaro |
| 6,117,174 A | | 9/2000 | Nolan |
| 6,123,705 A | | 9/2000 | Michelson |
| 6,129,763 A | | 10/2000 | Chauvin et al. |
| 6,165,219 A | | 12/2000 | Kohrs et al. |
| 6,176,882 B1 | | 1/2001 | Biedermann et al. |
| 6,206,922 B1 | | 3/2001 | Zdeblick et al. |
| 6,224,631 B1 | | 5/2001 | Kohrs |
| 6,325,827 B1 | | 12/2001 | Lin |
| 6,436,139 B1 | | 8/2002 | Shapiro et al. |
| 6,440,170 B1 | | 8/2002 | Jackson |

\* cited by examiner

Primary Examiner—David J. Isabella
(74) Attorney, Agent, or Firm—John C. McMahon (57) ABSTRACT

A convex spinal fusion interbody space device includes spaced apart superior and inferior abutment surfaces which are effectively medially convex. The peak of such convexity is displaced anteriorly of a central plane through the device. The spacer device has front to rear lateral concave surfaces and top to bottom lateral side channels that intersect with said convex surfaces. The spacer device has a height which is greater than the width of the device. The spacer device is implanted between a pair of adjacent vertebrae by insertion in a tipped-over orientation and then reoriented to an upright orientation for engagement by facing surfaces of the vertebrae. Fusion promoting bone material is packed between the vertebrae and about the spacer device subsequent to implantation.

20 Claims, 5 Drawing Sheets

SPINAL FUSION INTERBODY SPACER

BACKGROUND OF THE INVENTION

The present application is directed to an interbody device for implantation between a pair of adjacent vertebrae in order to provide support to the vertebrae and/or promote bone fusion between the vertebrae and, in particular, to an interbody device having opposed concave sides with a plurality of laterally opening side channels and a front to rear convex or trapezoidal side view for the upper and lower surfaces.

In the human spine the pad or disc between vertebrae is sometimes damaged or deteriorates due to age, disease, injury, or congenital defect. The vertebrae may also become compressed or otherwise damaged. Vertebrae often become too closely spaced anteriorly due especially to age, but also because of other factors that often produce an undesired abnormal curvature of the spine with respect to lordosis or kyphosis. Because of this, surgery is often utilized to place spacers or interbody devices between the vertebrae which provide proper spacing of the vertebrae and which also promote fusion between the vertebrae. When a device of this type is utilized for the purpose of promoting fusion, it is often referred to as a fusion cage or an intervertebral fusion device. When utilized to promote fusion, bone or bone fusion material is often placed about the interbody devices to promote growth of the bone between the vertebrae. In some procedures, multiple interbody devices are used together and bone fusion material is packed between the pair of devices that are placed in close proximity to one another and extending between the vertebrae to promote growth of bone and, therefore, fusion between the vertebrae.

In the past, interbody devices have typically been either generally rectangular or at least partially cylindrical and threaded. The cylindrical devices have an advantage in that they can be threadably received between and partially into the adjacent vertebrae. For this purpose, the vertebrae are typically first spaced apart, and then a drill is utilized to create a partial bore (radiused channel) in facing surfaces of opposed vertebrae which allows this type of interbody device to be received between the vertebrae. Because of the space between the bones, the interbody device usually engages the bones only along an upper surface and a lower surface of the device. When the interbody device is of a cylindrical threaded type, the upper and lower surfaces are radiused relative to a front to rear axis and such are essentially designed to engage the portion of the vertebrae where bone is removed by boring to create an opening for the device.

When interbody devices are used, it is desirable that such devices engage as much surface of bone as possible to provide support to the bone and to reduce the likelihood of subsidence of the device into the bone, resulting from contact pressure of the interbody spacer against an intervertebral surface of a vertebra. Subsidence can occur since part of the bone is somewhat spongy in nature, especially near the centers of the facing upper and lower surfaces of the vertebrae. The remainder of the structure of the intervertebral device mainly functions to support the two vertebral surfaces, unless the device is also used as a cage within or around which to pack bone fusion material. Because it is also desirable in such structures to maintain weight and volume as low as possible in order to make the device more compatible with the body, it is also desirable to make the entire device as small and lightweight as possible, while maintaining strength. Devices with passthrough windows and other open core structures are limited in strength because of substantial open regions in the core or body of the device.

It is also desirable to minimize the amount of cutting into and reshaping of the vertebral bones to only that which is necessary to correct the structure and function of the spine. Thus, it is desirable to conform an interbody spacer to the shape of the vertebral surfaces of adjacent vertebrae, which surfaces are shallowly concave, rather than conform the vertebrae to the shape of the interbody spacer.

As noted above, age and injury cause the vertebrae to somewhat anteriorly collapse over time. Therefore, it is also desirable for such an interbody spacer to correctly space the vertebrae anteriorly so as to promote normal lordosis or curvature with respect to the spine.

Still further, it is desirable to promote stability of the implant device by promoting bone growth thereabout.

SUMMARY OF THE INVENTION

The present invention provides an interbody or intervertebral spacer device for implantation between a pair of spaced, but adjacent, vertebrae. The spacer device is preferably generally convex or sloped between the anterior and posterior ends (that is, when viewed from the side, the device is convex between front and rear or along the longitudinal axis), preferably on both the top and bottom, so as to generally conform with the desired shape and positioning of the facing boney surfaces of the vertebrae that are engaged by the device. In particular, the spacer has mirror image convex inferior and superior bearing or abutment surfaces adapted to engage the somewhat concave end plate surfaces of adjacent vertebrae. Preferably, the top and bottom functional convexity of the spacer between front and rear or along the central axis thereof substantially matches the concavity of the vertebral end plate surfaces whereat the spacer is to be located during usage. In this manner maximum surface contact occurs and so that maximum support is provided to reduce the likelihood of subsidence, while encouraging normal lordosis of the spine. For this purpose, preferably the convexity of the abutment surfaces peaks at a location which is somewhat anterior of a medial or central plane between anterior and posterior end surfaces of the interbody spacer.

The abutment surfaces may be rounded and continuous or truly arced from front to rear or alternatively, the interbody spacer in some embodiments has faceted abutment surfaces, each formed by at least a peak surface, an anterior inclined surface, and a posterior inclined surface so as to form an overall functional convex arc as the engagement or abutment surface. The abutment surface may also include lateral bevels formed at lateral ends of the peak surface or other surfaces to facilitate implantation. Lateral side surfaces of the interbody spacer are preferably cylindrical and concave to reduce volume and weight and to produce arcs having good strength and support characteristics. The lateral surfaces have an axis that runs parallel to a front to rear axis of the device and each surface opens laterally outward along the entire length of the device.

Located on each lateral side of the spacer device is a plurality of side slots or channels which pass unobstructed from the inferior surface to the superior surface of the device. The side channels open laterally outward along the entire length thereof and preferably are interiorly radiused. Also, preferably the innermost portion of each channel generally intersects the innermost portion of the concave side or lateral surfaces of the spacer device.

The spacer device has a central body or core that is solid. The core is located between vertical planes that intersect with the innermost portion of the concave side surfaces as well as the inferior and superior surfaces and the core extends between anterior and posterior ends of the device. By the term "solid" is meant that the core is free of pass through apertures, bores, windows or the like that are drilled, machined or otherwise made in the core. It is noted that the core can be manufactured with materials such as human bone that has a certain amount of inherent porosity and still be considered solid as used herein. The core may also have shallow non-passthrough indents, knurling or grooves for tool gripping and likewise be considered solid as used herein.

The ends of the inferior and superior abutment surfaces are spaced apart by a nominal height dimension, while the lateral surfaces are separated at their closest by a nominal width or thickness dimension and at their widest by a maximum width dimension. The interbody spacer of the present invention preferably has a height dimension which is greater than the maximum width dimension. Because the mutually facing surfaces of the end plates of an adjacent pair of vertebrae are concave, the peripheral edges of adjacent vertebrae are closer spaced than central portions of the end plate surfaces.

The present invention includes a method of implanting interbody spacers comprising spreading the adjacent pair of vertebrae a distance somewhat greater than the width of the interbody spacer, insertion of the spacer into the intervertebral space in an orientation with the lateral surfaces of the spacer facing the end plates of the adjacent vertebrae and thereafter rotating of the spacer about a longitudinal axis to orient the abutment surfaces into facing relation relative to the end plates of the vertebrae. The vertebrae are then urged to seat on the abutment surfaces. During the process the position of the spacer may be adjusted as necessary and spinal fusion promoting bone material positioned between the vertebrae and within the central opening. In some methods of use, only a single spacer is used with other posterior implant support structure. In other circumstances, it is desirable to implant at least a pair of laterally spaced interbody spacers between the vertebrae for stability and strength.

Preferably, the spacer is used in conjunction with other implants including bone screws that are implanted in the vertebrae. The bone screws are tightly secured near the end of the procedure to a rod or rods that extend along the spine. The bone screws and, consequently, the associated vertebrae are positioned at the end of the intervertebral device insertion procedure so as to urge the vertebrae into engagement with the device and thereby secure the position of the device and help or cooperate with the device to favorably adjust the lordosis of the vertebrae, while securely locating the adjacent vertebrae relative to one another so as to promote fusion.

Interbody devices of the type used herein must be compatible with implantation in the human body. Such devices include biologically active implants such as made of boney material, coral or other biologically active material) where the vertebral bone grows through the material of the implant and over time replaces part or all of the implant by creeping substitution and biologically inactive materials such as metals, plastics and the like.

OBJECTS AND ADVANTAGES OF THE INVENTION

Therefore, the objects of the present invention include: providing an interbody spacer or fusion cage device having convex upper and lower bearing or abutment surfaces for implanting between a pair of adjacent vertebrae to properly space the vertebrae and/or to promote fusion between the vertebrae; providing such a device in which the peak of convexity of the abutment surfaces is positioned somewhat anterior of a medial plane midway between anterior and posterior surfaces of the spacer; providing such a device in which the convex abutment surfaces are formed by planar facets, including at least a peak facet, an anterior inclined facet, and a posterior inclined facet, all cooperating as a single unit or unitary piece so as to produce a functional curve; providing such a device formed of a material which is appropriate to the long term disposition of the device desired, such as a biologically inactive metallic material, a biologically inactive non-metallic material, a biologically active bone-based material, or a biologically active non-bone-based material; providing such a device having cylindrically concave lateral or side surfaces that join the upper and lower abutment surfaces on opposite lateral sides of the device; providing such a device having a plurality of side channels opening onto each concave lateral side surface and being laterally outward open along the entire length thereof between inferior and superior surfaces of the device; providing such a device wherein the structure of the interbody spacer device is strong, while minimizing volume and weight; providing a device having a solid central core or body; providing such a device which enables relatively close spacing of a pair of devices in side by side relationship; providing such a device that enables positioning in use so as to produce a substantial opening between a pair of devices in side by side relationship to facilitate packing with bone chips and subsequent fusion between the vertebrae associated with the devices; providing such an interbody spacer device which minimizes surgical alteration of the vertebral bones between which the spacer is implanted; providing a method of implanting such a device between a pair of adjacent vertebrae including spreading the adjacent vertebrae apart a distance somewhat greater than the lateral width of the spacer, insertion of the spacer between the vertebrae in a laterally tipped over orientation, and rotating so as to reorient the spacer to an upright position to engage the upper and lower abutment surfaces with facing end plate surfaces of the adjacent vertebrae and thereafter using other implants to urge the posterior ends of the vertebrae toward one another so as to effectively clamp the device in place between the vertebrae; and to provide such a device which is economical to manufacture, which is relatively simple to implant, which is efficient in operation, and which is particularly well suited for its intended usage.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figures 1, 2:
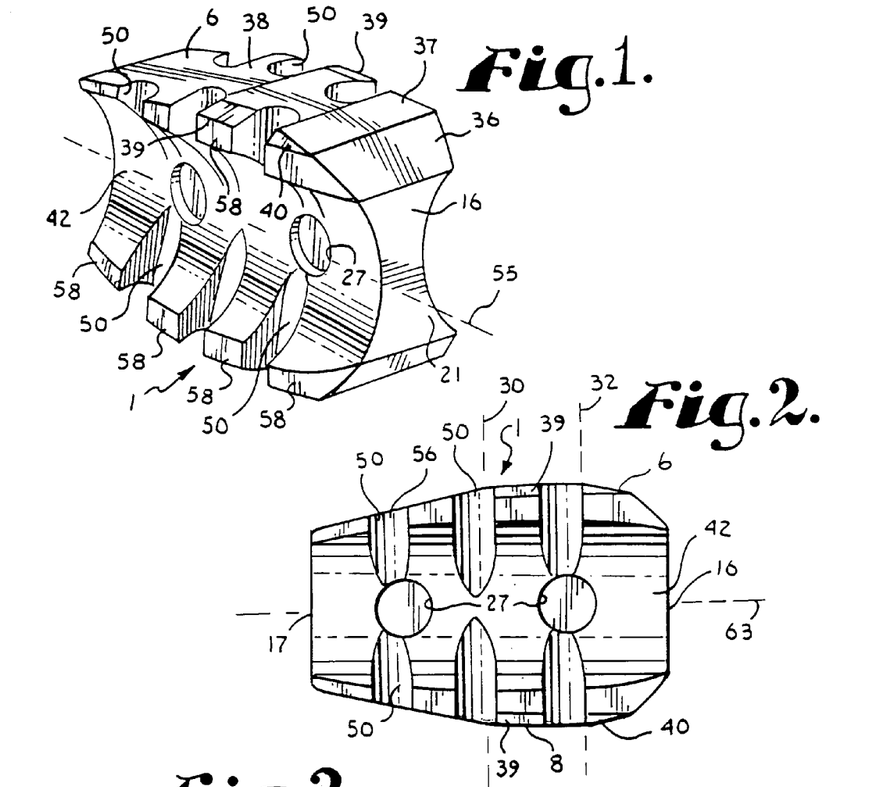
FIG. 1 is an enlarged perspective view of a convex spinal fusion interbody spacer device embodying the present invention.
FIG. 2 is a side elevational view of the spacer device.

The reference numeral 1 generally designates a convex spinal fusion interbody spacer device which embodies the present invention. The device 1 is used to maintain proper spacing between a pair of adjacent vertebrae 3 and 4 of a human spine as a replacement for the intervertebral disc and to promote fusion between the vertebrae 3 and 4, preferably in conjunction with other implants, as noted below. In particular, the device 1 has a superior (or upper) surface 6 and an inferior (or lower) surface 8 which surfaces 6 and 8 are arced or convex or effectively convex when viewed from the side, such as is seen in FIG. 2. The convexity of the abutment or bearing surfaces 6 and 8 is fixed or rigid and conforms to the natural concavity of the mutually facing surfaces 10 and 12 of end plates of the adjacent vertebrae 3 and 4. The device 1 is constructed from a single, unitary and rigid blank or molded structure and has a fixed shape that is medially bowed outwardly at the top and bottom, preferably forward of a front to rear center of the device 1, as discussed below. In some embodiments the device 1 is tear shaped, fish shaped or fusiform in nature.

Figures 6, 7:
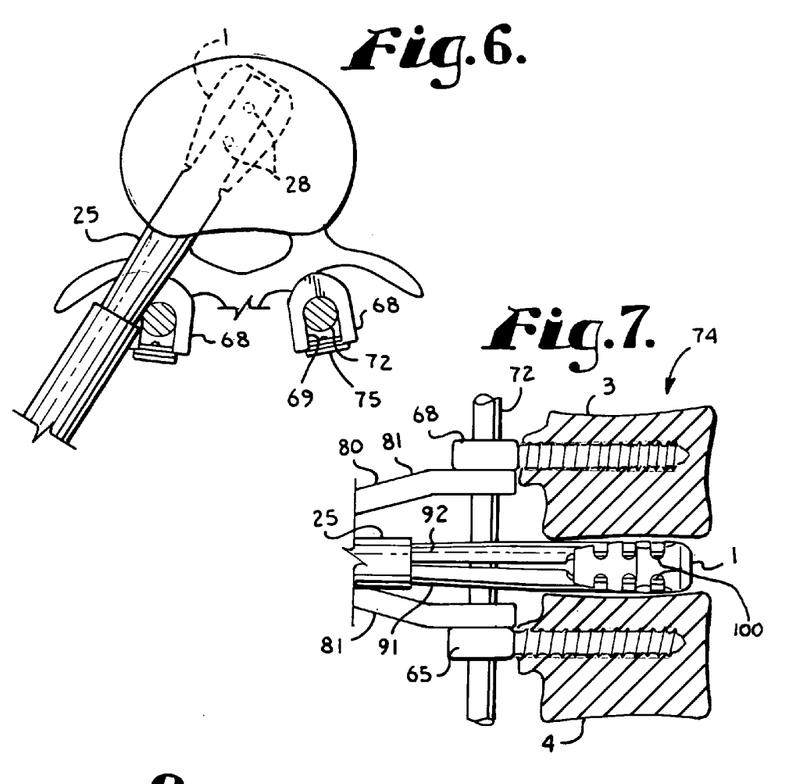
FIG. 6 is a top plan view of the spacer device being inserted between two vertebrae utilizing a tool, with the spacer turned on the side thereof.
FIG. 7 is a fragmentary side elevational view of the spacer device and vertebrae in the position shown in FIG. 6 with the spacer device in a laterally tipped over orientation between the adjacent pair of the vertebrae, with portions removed to show detail thereof.

The illustrated spacer device 1 includes front and back walls or sections 16 and 17. The front wall 16 and back wall 17 have respective anterior and posterior outer end surfaces 21 and 23. The end surfaces 21 and 23 are illustrated as planar, although it is foreseen that they could be an alternative shape. The illustrated spacer device 1 includes tool engagement formations to enable positive engagement by an installation tool 25 (FIGS. 11, 6 and 7), such as tool indents 27 that do not pass through the device 1 and that provide a shallow location for the tool 35 to grip with mating projections 28. The depth of the indents 27 is preferably about 1 millimeter. Alternatively, it is foreseen that other structure such as knurling, channels or the like could be utilized to enhance a tool grip.

The preferred spacer device 1 of the present invention is not symmetrical, when viewed from either side. FIG. 2 illustrates a front to rear middle plane 30 positioned halfway between the end walls 16 and 17 and parallel thereto, which bisects the device 1 from front to back with the front or anterior end thereof being to the right in FIG. 2. Also illustrated is a "convexity" plane 32 positioned at a medial location where there is peak convexity of the abutment surfaces 6 and 8, thus, indicating the location of such peak convexity. The imaginary convexity plane 32 is located in spaced relationship to the end walls 16 and 17 such that the vertical height of the device 1 at the location of the plane 32 is greater than the height of either end surface 21 or 23. In the illustrated embodiment the height of the end surfaces 21 and 23 is essentially the same, although it is foreseen that one may have a greater height than the other, especially the front end surface 21 may have a height greater than the rear end surface 23.

As illustrated, the convexity plane 32 is positioned closer to the anterior end surface 21 (about 25% of total length from anterior end to plane 32) than to the posterior end surface 23 and is, thus, spaced anteriorly of the middle plane 30. The reason for the anteriorly shifted or displaced asymmetry of the convexity of the device 1 is so that the abutment surfaces 6 and 8 more closely conform to the concavity of the vertebral end plate surfaces 10 and 12, preferably so as to produce a correct lordotic alignment of the vertebrae 3 and 4 when implanted. Such shape conformance between the abutment surfaces 6 and 8 and the vertebral surfaces 10 and 12 tends to maximize bearing engagement therebetween and tends to minimize possible subsidence of the device 1 into the vertebrae 3 and 4, while providing greater spacing between the anterior ends of the vertebrae 3 and 4 than the posterior ends thereof (see FIG. 8).

The illustrated abutment surfaces 6 and 8 are formed by multiple component surfaces or facets, including a peak facet 35, an anterior or front facet 36, an intermediate facet 37 between the front facet 36 and peak facet 35 and a posterior or rear facet 38 with the bottom being a mirror image of the top. However, it is foreseen in certain circumstances that the surfaces 6 and 8 may be formed by a continuous or even discontinuous curved surface or by other suitable elements forming a surface that will generally and functionally conform to the concavity of the lower and upper surface of the vertebrae 3 and 4 respectfully. The surfaces 6 and 8 may also include lateral facets or bevels 39 and 40. In certain embodiments it is foreseen that the sides of the superior and inferior surfaces 6 and 8 may be curved or radiused to meet the lateral sides of the device 1 to promote ease of rotation during installation. Because the plane of convexity 32 is displaced anteriorly of the middle plane 30, the combined length of the anterior facet 36 and intermediate facet 37 is shorter than the posterior facet 38.

As noted above the illustrated abutment surfaces 6 and 8 are faceted, but such could alternatively be formed by continuous, curved surfaces. In the faceted surfaces the edges 41 formed by intersection of the facets 35–38 provide a small measure of gripping engagement with the vertebral surfaces 10 and 12 to hold the devices 1 in place and in the desired orientation between the adjacent vertebrae 3 and 4 until fusion between the vertebrae 3 and 4 occurs. Additionally, the abutment surfaces 6 and 8 are somewhat more easily and more accurately formed by the facets 35–38 in a machining process than would be possible with a compound curved contour of the surfaces 6 and 8.

Figure 3:
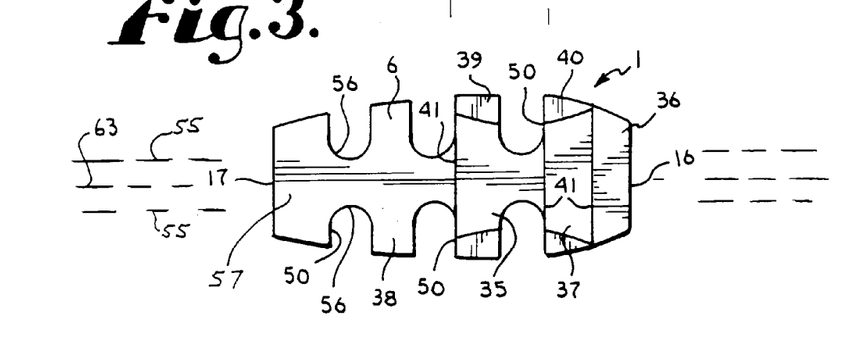
FIG. 3 is a top plan view of the spacer device.

Referring to FIGS. 1 and 3, the interbody spacer device 1 has side or lateral surfaces 42 and 43. Although it is foreseen that the side surfaces could have other shapes in certain embodiments, the illustrated side surfaces 42 and 43 are inwardly cylindrical or concave and extend parallel to the longitudinal or front to rear axis so as to produce upper and lower arcs 44 to provide substantial strength requiring relatively little physical space. In particular, the concavity of the surfaces 42 and 43 results in a weight reduction in the device 1 without appreciably reducing its strength, apparently due to the arches and the fact that such arcs are less likely to create stress risers in the device 1. Additionally, the concave shape leaves more volume between the adjacent vertebrae 3 and 4 to receive fusion promoting bone material.

In the illustrated embodiment a series of side slots or channels 50 are formed on each side of the device 1 so as to pass between the superior surface 6 and the inferior surface 8 while opening laterally outward along the entire length thereof to a respective side. Each of the side channels 50 open onto a respective lateral surface 42 or 43. The innermost part of each channel 50 preferably intersects with an axis 55 which rests on the center of the convex surfaces 42 and 43 at the innermost portion thereof and which extend parallel to a central axis 63 of the device 1.

Each channel 50 is substantially wider than a thread and is preferably about one eighth of the length of the device 1 in width with radiused innermost ends 56. The channels 50 define feet 58 on either side thereof that extend laterally outward from the top and bottom of both sides of the device 1 as part of the arcs 44, so as to form a vertebra support matrix while allowing bone growth around the outside of the device through the channels 50.

The device 1 has a central body or core 57 that is located between superior and inferior surfaces 6 and 8, between end walls 16 and 17 and between vertical planes passing through axis 55. The core 57 is free of pass through bores, windows or the like but may include tool gripping apertures 27, so as to form a solid and relatively strong central structure for the device 1.

The device 1 can be formed from any material which has suitable structural properties, which is biologically non harmful, and which does not promote the growth of pathogens. The material of construction can be biologically active or inactive as discussed in greater detail below. For example, various types of metal are suitable as materials of construction. In the illustrated embodiment, the device 1 is formed of polymer polyester ketone (commonly known as "peek"). Composites are also available which satisfy the structural and biological requirements. The device 1 can be formed by molding, by machining, cutting, or the like, or by a combination of such processes to preferably form a single or unitary and substantially rigid structure, preferably with no parts that are moveable relative to other parts thereof.

Figure 4:
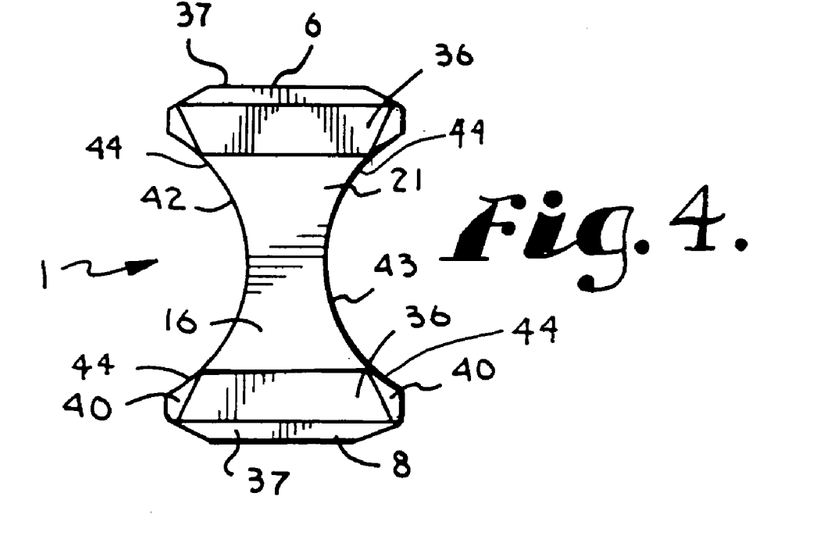
FIG. 4 is front elevational view of the spacer device.
Figure 5:
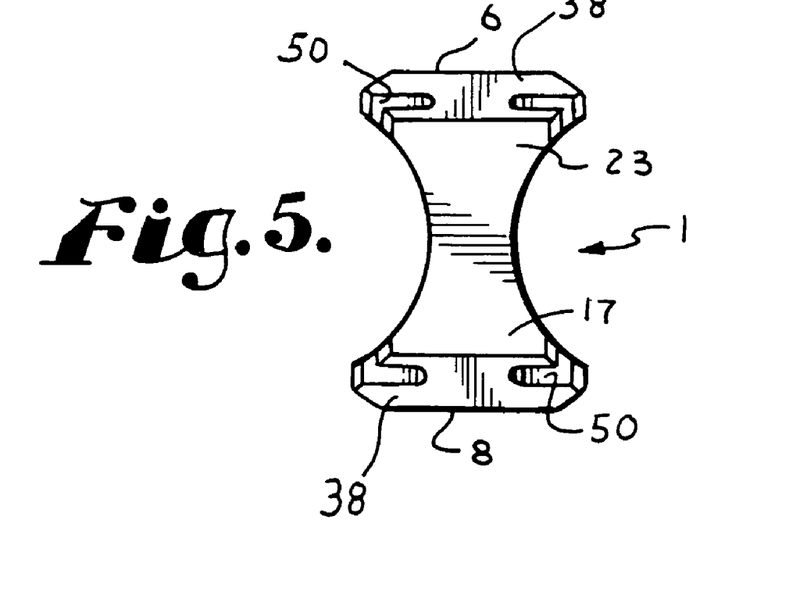
FIG. 5 is a rear elevational view of the spacer device.

Also disclosed are methods of implanting a spinal fusion spacer device 1 between a pair of adjacent vertebrae 3 and 4. Referring to FIG. 4, the device 1 has a maximum height dimension measured between the upper and lower peak facets 35 and a maximum width or thickness dimension which is the widest side to side dimension. As can be observed from the frontal view shown in FIG. 4, the height dimension of the device 1 exceeds its minimum and maximum width by a considerable extent. In the illustrated embodiment the height at plane 32 is about 1.5 times the maximum side to side width. It should be noted that the upright orientation of the device 1 shown in FIGS. 1–5 and 8–10 is the operational orientation of the spacer device 1 in which the device 1 performs the function of spacing between the vertebrae 3 and 4.

As stated previously, the facing surfaces 10 and 12 of the vertebrae 3 and 4 are somewhat concave in that most of the interior or central regions 60 (FIG. 10) of the surfaces 10 and 12 are spaced farther apart than edge regions 61 of the surfaces 10 and 12. In order to implant a device 1 between the vertebrae 3 and 4, it is preferable to position the vertebrae 3 and 4 far enough apart so that the device 1 can be inserted therebetween at least sideways, in the alignment shown in FIG. 6. Insertion is most often by a posterior approach, but may be from any direction selected by the surgeon. In the present embodiment, the vertebrae 3 and 4 are spread apart during the surgical procedure a sufficient distance that the device 1 can be inserted between the edge regions 61 in a laterally laid-over or tipped-over orientation (see FIGS. 6 and 7) and then rotated to the upright orientation shown particularly in FIGS. 1, 4, and 9. The device 1 is inserted between the vertebrae 3 and 4 in a tipped-over orientation and urged by the tool 25 to the eventual use location thereof and then rotated only ninety degrees (as opposed to screwing completely into place) about the longitudinal axis 63.

More specifically, with respect to the procedure and referring to FIGS. 6–9, a pair of open-headed bone screws 68 are threadedly implanted into each of the vertebrae 3 and 4. Open heads 69 of the screws 68 are aligned to receive spinal fixation rods 72 which run lengthwise along at least a portion of the spine 74 of which the vertebrae 3 and 4 are components. The bone screw heads 69 receive closure plugs 75 which, when tightened, secure the rods 72 within the heads 69. The heads 69 and plugs 75 may employ cooperating helical guide and advancement mechanisms to advance the plugs 75 into engagement with the rods 72, as the plugs 75 are rotated into the heads 69. Details of open-headed bone screws 68 and closure plugs 75 which would be appropriate for use with the device 1 can found in U.S. Pat. No. 6,004,349, which is incorporated herein by reference. Initially the rods 72 are captured only loosely in the heads 69 by the plugs 75, so as to allow movement of the screws 68 along the rods 72 under control of the surgeon.

The vertebrae 3 and 4 are spaced a desired distance by use of a commonly used type scissors tool 80 (partially seen in FIG. 8) with spreader arms 81, and the plugs 75 may be lightly tightened in the bone screws 68. At this point in the procedure, the desired intervertebral distance is such a distance which enables insertion of the spacer device 1 between the vertebrae 3 and 4 in the tipped-over orientation (FIGS. 6 and 7) and then the device 1 is uprighted (FIG. 8) by ninety degree rotation and reorientation to the upright orientation with the tool 25. In particular, the spacer device 1 is inserted between the spread vertebrae 3 and 4 in the tipped-over orientation and rotated to the upright orientation using the installation tool 25; then the tool 25 is detached from the device 1 and removed from the site of the surgical procedure.

Figure 11:
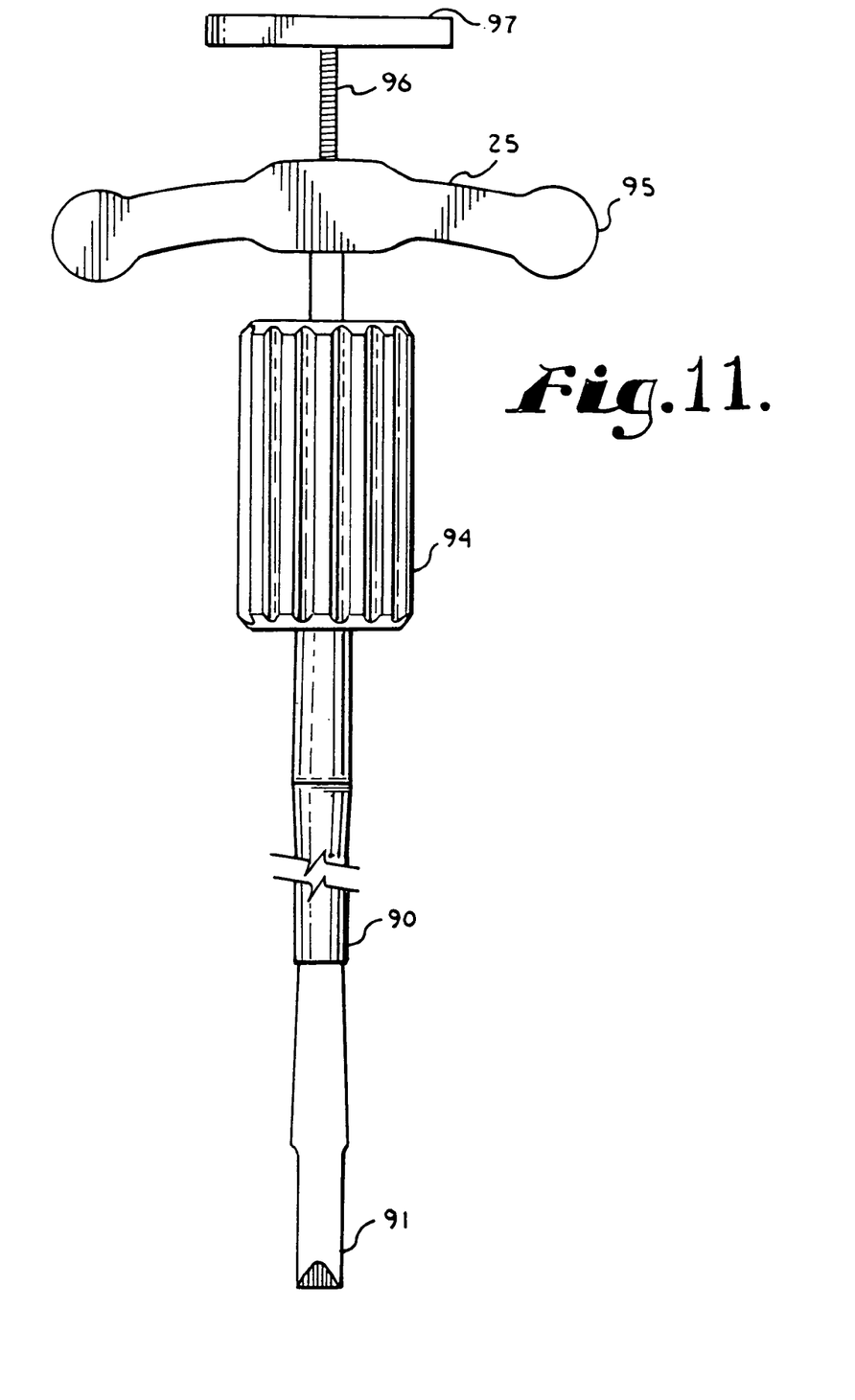
FIG. 11 is a side elevational view of the spacer device implant tool.

The tool 25 has an elongate shaft 90 with a pair of flexible side-by-side arms 91 and 92 located in the shaft 90. The arms 91 and 92 expand near a device engaging end thereof and the shaft 90 can be screwed down a part of the length of the arms 91 and 92 to squeeze the arms 91 and 92 together by rotation of a grip 94. A T-handle 95 allows the surgeon to grip the tool 25. An elongate pusher rod 96 extends the length of the shaft 90 and is threadably received therein. The pusher rod 96 is rotated by a handle 97 that allows a surgeon to advance the pusher rod 96 along the interior of the shaft 90 to dislodge the device 1, if required to separate the device 1 from the tool 25. Each arm 91 has an inner surface 100 sized and shaped to be received in the convex lateral surfaces 42 and 43 of the device 1 with the projections 28 thereon located in the device indents 27.

Figure 8:
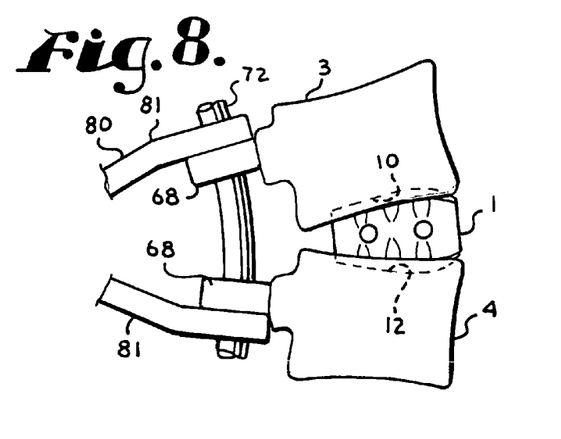
FIG. 8 is a fragmentary side elevational view illustrating the spacer device in an upright position between the vertebrae.
Figure 9:
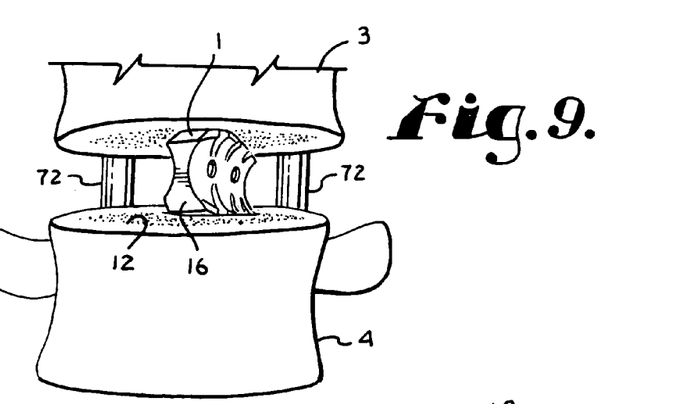
FIG. 9 is a front elevational view of the spacer device in the final upright position of FIG. 8 and located between the adjacent vertebrae.

The plugs 75 which are lightly tightened during the device implantation procedure are then loosened and the tool 80 (see FIG. 8) is reversed from the earlier procedure and is used to urge the screws 68 of adjacent vertebrae 3 and 4 toward each other, so that the posterior ends of the vertebrae 3 and 4 become more closely spaced to allow the inner surfaces 10 and 12 respectively thereof to snugly engage the superior and inferior abutment surfaces 6 and 8 of the device 1, preferably in a clamping relationship, as seen in FIG. 8. This clamping secures the device 1 in the desired position selected therefor between the vertebrae 3 and 4. The angular orientation of the device 1 about an axis parallel to the spine 60 is adjusted, if necessary prior to final tightening of the plugs 75 to lock the relative position between a respective rod 72 and screws 68. Prior to insertion or after insertion in the bone screws 68, the rods 72 may be bent somewhat to achieve a desired angular or lordotic relationship between the vertebrae 3 and 4. A single device 1 when used in conjunction with a pair of bone screws 68 in each vertebrae 3 and 4 forms a solid multiple point of support structure so as to stabilize the vertebrae 3 and 4 with respect to each other. In the illustrated embodiment there is a stable three point support (two bone screws 68 and the device 1) provided for each vertebrae 3 and 4 relative to its adjacent vertebrae 3 or 4.

Figures 10, 12:
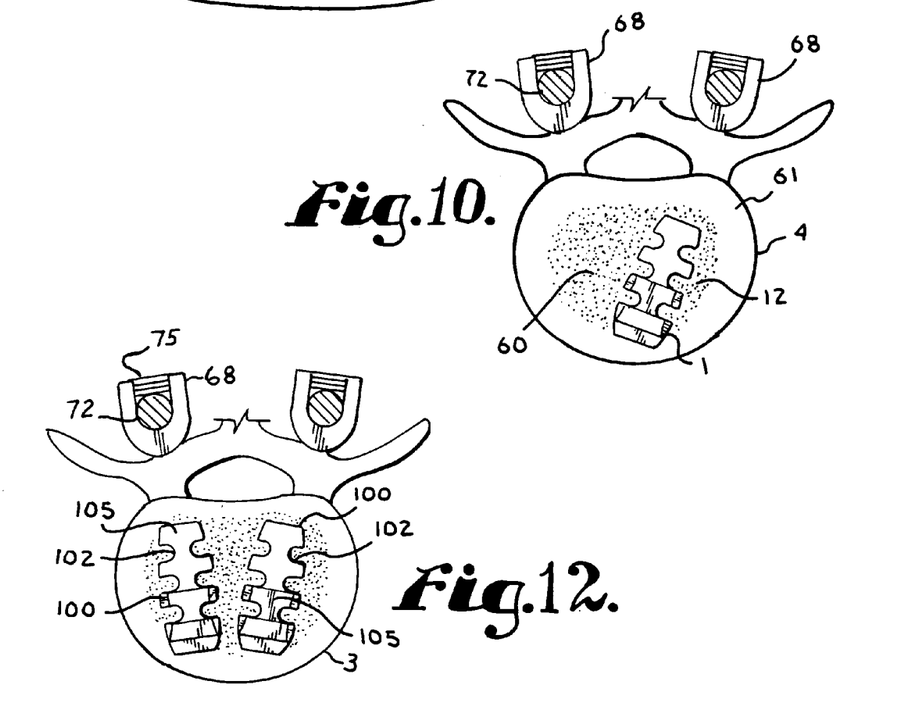
FIG. 10 is a top plan view of the spacer device shown positioned on one of a pair of vertebrae in the upright position.
FIG. 12 is a top plan view of a modified embodiment showing a pair of the interbody spacer devices located on one of a pair of vertebrae.

In an alternative usage, the implantation procedure may also include the insertion of a pair of spacer devices 100, such as is shown in FIG. 12 between the vertebrae 3 and 4 wherein the devices are preferably laterally spaced and aligned in a non parallel configuration. The pair of devices 100 are aligned to be closer anteriorly than posteriorly. Each of the devices 100 have side channels 102 and top and bottom engagement surface 105 that engage respective vertebra 106, as discussed before with respect to the device 1.

When the desired degree of engagement between the vertebrae 3 and 4 and the two devices 100, along with the desired orientation of the devices 100 relative to the vertebrae 3 and 4 is achieved, the closure plugs 75 are advanced into secure engagement with the rods 72 in a substantially permanent relation. Such an embodiment, as seen in FIG. 12, provides four points of support for each vertebrae 3 and 4 relative to the adjacent vertebrae 3 or 4.

Any voids between the vertebrae 3 and 4 and adjacent the device 1 or devices 100 are preferably packed with bone material which, over time, will promote fusion between the vertebrae 3 and 4, so that the vertebrae 3 and 4 will eventually be locked in the spacing and orientations established by the spacer device 1 or devices 100 and the rods 59.

The devices 1 and 100 preferably include no moving or adjustable parts, are non-threaded, and include no fins on the upper and lower surfaces thereof to cut into the bone.

The devices 1 and 100 may be manufactured from biologically inactive materials or from biologically active materials which are compatible with implantation. The devices 1 and 100 formed of biologically inactive materials are chemically and biologically essentially inert in their implanted environments. Fusion of the vertebrae 3 and 4 occurs around the devices 1 and 100 and through respective side channels 50 and 102 formed through into the sides of the devices 1 and 100 respectively; however, the devices 1 and 100 remain intact after implantation. The biologically inactive materials used for the devices 1 and 100 can be divided into metallic materials and non-metallic materials.

Metallic biologically inactive materials may include certain stainless steel alloys, titanium, and tantalum and other alloys which are structurally, chemically, and biologically appropriate. Non-metallic biologically inactive materials for the devices 1 and 100 can include certain plastics or polymers, organic and inorganic resins, composites, and ceramics, especially polyester ketone or the polymer commonly referred to as "peek". The polymers are preferably non-porous. The composites may include carbon fiber reinforced materials. Appropriate ceramics are preferably porous and can be of an "open scaffold" type which allow bone fusion growth through the ceramic material itself.

The devices 1 and 100 can also be formed from biologically active materials which are normally biologically substituted for, absorbed, or otherwise replaced as bone fusion of the vertebrae 3 and 4 proceeds. The biologically active materials can be either bone-based or non-bone-based. The term bone-based material is used herein to refer to a material which is made from actual bones, bone derivatives, or materials which are chemically bone-like. Bones are typically formed mostly (about 85 percent) of tri-basic calcium phosphate which, in living bone, is called hydroxy-apatite or simply calcium phosphate. In general, the bone is formed by cutting, machining or the like or bone derived material is ground, mixed with a suitable resin or other binder, and cast, molded or machined to shape. Further machining or other mechanical forming may be performed in final shaping of formed implant spacers. The source of bone for such material is possibly a harvest from another part of the patient who will receive the implant or from cadaver bone or allograft. Other sources may include non-human bone.

Biologically active, non-bone-based materials appropriate for use in the devices 1 and 100 include corals, certain resins and similar materials. The principal constituent of coral is calcium carbonate in a porous form which allows bone fusion growth through the resulting spacer. The devices 1 and 100 can be formed of coral by machining or carving processes. The coral material is normally replaced over time by biological processes in the body, as the spinal fusion process occurs.

Although the illustrated embodiment shows the devices 1 and 100 being inserted fully from the posterior and then rotated ninety degrees, it is foreseen that the devices 1 and 100 could be inserted anteriorly or from the side.

It is also foreseen that in certain embodiments, the greatest height of the device may be at an anterior end thereof, as required in some situations to produce correct spinal curvature, such that the device has a generally trapezoidal side profile.

It is to be understood that while certain forms of the present invention have been illustrated and described herein, it is not to be limited to the specific forms or arrangement of parts described and shown.

What is claimed and desired to be secured by Letters Patent is as follows:

1. A spinal fusion interbody spacer comprising:
 a) a body having superior and inferior abutment surfaces sized and shaped to be adapted to abut against adjacent spaced vertebrae;
 b) said body having concave lateral side surfaces; and
 c) at least one side channel extending between said inferior and superior abutment surfaces and opening laterally onto each lateral side surface.

2. The spacer according to claim 1 wherein:
 a) a plurality of side channels opens onto each lateral side surface.

3. The spacer according to claim 2 wherein:
 a) there are at least three side channels associated with each lateral side surface.

4. The spacer according to claim 1 wherein:
 a) a width of each side channel is approximately one eighth the front to rear length of said spacer.

5. The spacer according to claim 1 wherein:
 a) said spacer has a solid central core that is free of pass through openings.

6. The spacer according to claim 1 wherein:
 a) said side channels innermost portion generally intersects with said lateral side surfaces innermost portion.

7. The spacer according to claim 1 wherein:
 a) said side surfaces include at least one shallow and non pass through tool gripping indent.

8. The spacer according to claim 1 wherein:
 a) said inferior and superior surfaces are each functionally curved to form a curved structure from an anterior end to a posterior end of said spacer.

9. The spacer according to claim 8 wherein:
 a) said curved structure is convex and formed by placement of discrete planar facets.

10. The spacer according to claim 8 wherein:
 a) said curved structure is highest between a center and said anterior end of said spacer.

11. In an interbody spacer having a body with superior and inferior surfaces and a pair of lateral side surfaces; the improvement comprising:
 a) each of said lateral side surfaces being concave and at least one side channel for each side surface extending between said inferior and superior surfaces and opening laterally outward onto respective side surfaces; each side channel opening laterally outward along the entire length thereof.

12. The spacer according to claim 11 wherein:
 a) said side surfaces are and have an axis associated therewith that extends parallel to a front to rear central axis of said spacer.

13. The spacer according to claim 12 wherein:
 a) an innermost portion of each side channel generally intersects an innermost portion of a respective side surface.

14. The spacer according to claim 12 wherein:
 a) there are a plurality of side channels that open onto each side surface.

15. The spacer according to claim 14 wherein:
 a) there are at least three side channels associated with each side surface.

16. The spacer according to claim 12 wherein:
 a) each side channel has a width that is approximately one eighth the anterior to posterior length of said spacer.

17. A method of providing intervertebral support for a patient comprising the steps of:
 a) providing a vertebral spacer having concave lateral side surfaces and being sized and shaped to be positioned between a pair of vertebrae;
 b) placing at least one lateral side channel on each lateral side of said spacer so as to intersect with said concave lateral side surfaces wherein each said side channel runs from the top to the bottom of the spacer and opens laterally outward along the entire length of said side channel;
 c) placing said spacer between a pair of vertebrae; and
 d) allowing bone growth through said side channels to promote spacer stability.

18. A spinal fusion interbody spacer comprising:
 a) a body having superior and inferior abutment surfaces sized and shaped to be adapted to abut against adjacent spaced vertebrae;
 b) said body having lateral side surfaces; said side surfaces are arced and concave having a central axis extending from front to rear; and
 c) at least one side channel extending between said inferior and superior abutment surfaces and opening laterally onto each lateral side surface.

19. A spinal fusion interbody spacer comprising:
 a) a body having superior and inferior abutment surfaces sized and shaped to be adapted to abut against adjacent spaced vertebrae;
 b) said body having lateral side surfaces; and
 c) at least one side channel extending between said inferior and superior abutment surfaces and opening laterally onto each lateral side surface; each of said side channels being curved at an innermost end thereof so as to have a radius of curvature extending between the inferior and superior abutment surfaces.

20. A spinal fusion interbody spacer comprising:
 a) a body having superior and inferior abutment surfaces sized and shaped to be adapted to abut against adjacent spaced vertebrae;
 b) said body having at least one concave lateral side surface; and
 c) at least one side channel extending between said inferior and superior abutment surfaces and opening laterally onto said lateral side surface.

* * * * *